US008853918B2

(12) United States Patent
Krohn et al.

(10) Patent No.: US 8,853,918 B2
(45) Date of Patent: Oct. 7, 2014

(54) TRANSDUCER STRUCTURE FOR A TRANSDUCER PROBE AND METHODS OF FABRICATING SAME

(75) Inventors: Matthew Harvey Krohn, Lewistown, PA (US); Prabhjot Singh, Guilderland, NY (US); Paul Aloysius Meyer, McVeytown, PA (US); Wei Luo, Lewistown, PA (US)

(73) Assignee: General Electric Company, Schenectady, NY (US)

( * ) Notice: Subject to any disclaimer, the term of this patent is extended or adjusted under 35 U.S.C. 154(b) by 469 days.

(21) Appl. No.: 13/240,754

(22) Filed: Sep. 22, 2011

(65) Prior Publication Data

US 2013/0076207 A1  Mar. 28, 2013

(51) Int. Cl.
| | |
|---|---|
| *H01L 41/08* | (2006.01) |
| *H01L 41/22* | (2013.01) |
| *H01S 4/00* | (2006.01) |
| *H04R 31/00* | (2006.01) |
| *A61B 8/14* | (2006.01) |
| *H04R 17/00* | (2006.01) |
| *G01N 29/24* | (2006.01) |
| *B06B 1/06* | (2006.01) |
| *H01L 41/37* | (2013.01) |
| *H01L 41/18* | (2006.01) |

(52) U.S. Cl.
CPC ............ *H01L 41/183* (2013.01); *G01N 29/245* (2013.01); *B06B 1/0622* (2013.01); *H01L 41/37* (2013.01)
USPC ........... 310/334; 29/25.35; 29/592.1; 29/594; 600/459; 367/155

(58) Field of Classification Search
USPC ................. 310/333–336, 357, 358; 29/25.35, 29/592.1, 594; 600/459; 367/155
See application file for complete search history.

(56) References Cited

U.S. PATENT DOCUMENTS

| | | | | |
|---|---|---|---|---|
| 4,518,889 | A | * | 5/1985 | 'T Hoen .......................... 310/357 |
| 4,658,176 | A | * | 4/1987 | Nakaya et al. ................. 310/334 |
| 4,828,961 | A | * | 5/1989 | Lau et al. ....................... 430/198 |
| 5,648,942 | A |   | 7/1997 | Kunkel, III |
| 6,117,612 | A |   | 9/2000 | Halloran et al. |
| 6,984,922 | B1 | * | 1/2006 | Nagahara et al. ............. 310/334 |
| 7,088,432 | B2 |   | 8/2006 | Zhang |
| 7,449,821 | B2 |   | 11/2008 | Dausch |
| 7,652,410 | B2 | * | 1/2010 | Prus ............................... 310/334 |
| 8,212,456 | B1 | * | 7/2012 | Moore et al. ................... 310/358 |
| 2001/0042291 | A1 | * | 11/2001 | Esashi et al. .................. 29/25.35 |
| 2005/0259785 | A1 | * | 11/2005 | Zhang ............................. 378/34 |
| 2008/0252179 | A1 | * | 10/2008 | Kimura et al. ................. 310/365 |
| 2009/0199392 | A1 |   | 8/2009 | Singh et al. |
| 2009/0230823 | A1 | * | 9/2009 | Kushculey et al. ........... 310/366 |
| 2010/0217160 | A1 | * | 8/2010 | Saguchi et al. ................... 601/2 |

FOREIGN PATENT DOCUMENTS

JP          11-112048 A  *  4/1999  ............... B41J 2/045

* cited by examiner

*Primary Examiner* — Thomas Dougherty

(74) *Attorney, Agent, or Firm* — Fletcher Yoder, P.C.

(57) ABSTRACT

A composite ceramic transducer structure for use in the construction of an ultrasound probe includes a substrate and a plurality of piezoelectric transducer posts. The plurality of piezoelectric transducer posts are controllably formed on the substrate in a plurality of spatial positions located on an X-Y plane of the substrate. The plurality of piezoelectric posts includes a plurality of shapes defined in an X-Y-Z plane of the substrate, wherein the plurality of piezoelectric transducer posts are configured to facilitate minimizing shear waves within the ultrasound probe.

20 Claims, 9 Drawing Sheets

TRANSDUCER STRUCTURE FOR A TRANSDUCER PROBE AND METHODS OF FABRICATING SAME

BACKGROUND OF THE INVENTION

The embodiments described herein relate to transducer structures, and more particularly, to methods and systems for a controlled formation and arrangement of a transducer structure for use in transducer probes.

Ultrasonic probes, which often include a piezoelectric post or an array of piezoelectric posts, are used in several applications, including the nondestructive imaging of the interior of structures by, for instance, ultrasound scanning. In many such imaging applications, it is desirable to use a composite material, which is usually comprised of a piezoelectric material and a non piezoelectric material. These composite materials result in better piezoelectric performance as compared to monolithic piezoelectric materials. It is necessary to reduce the size of the individual piezoelectric features, which constitute the composite, as much as possible, to enable operation at higher frequencies, which in turn provides increased resolution in the obtained image. Known dice-and-fill methods for manufacturing piezoelectric transducers generally reach a resolution limit when columnar posts in the piezoelectric transducers are reduced in size. Moreover, known methods of manufacturing probes, such as dice-and-fill methods, are limited to the fabrication of straight line kerfs between transducer posts, thereby restricting the available transducer design space, e.g. limits of transducer post arrangements, cross-sectional shapes and the inability to make free-form three-dimensional transducer features.

Operation of known ultrasound probes at higher frequencies is achieved in part by decreasing the thickness of the transducer material and correspondingly reducing the x-y cross-sectional area of the piezoelectric posts comprising the transducer. This operation results in an increase in the dicing time to complete the manufacturing of the transducer. Moreover, the production yield of the dice-and-fill method for manufacturing high-frequency transducers is generally reduced as compared to the production yield of conventionally manufactured lower-frequency transducers due to the increased likelihood of breakage of the (thinner) piezoelectric posts. Additionally, known manufacturing methods may produce transducers fabricated with shear waves that cause one or more ultrasound wavelengths to travel within the composite structure. Shear waves result in design constraints for probes and result in acoustical interferences such as ringing in probes.

BRIEF DESCRIPTION OF THE INVENTION

In one aspect, a composite ceramic transducer structure for use in the construction of an ultrasound probe is provided. The structure includes a substrate and a plurality of piezoelectric transducer posts. The plurality of piezoelectric transducer posts are controllably formed on the substrate in a plurality of spatial positions located on an X-Y plane of the substrate. The plurality of piezoelectric posts includes a plurality of shapes defined in an X-Y-Z plane of the substrate, wherein the plurality of piezoelectric transducer posts are configured to facilitate minimizing shear waves within the ultrasound probe.

In another aspect, a method for manufacturing a ceramic transducer structure for use in the construction of an ultrasound probe is provided. The method includes forming a substrate layer and forming a layer on the substrate layer, wherein the layer includes a transducer material and a photopolymer. The method further includes exposing a plurality of selected regions of the layer to a programmable light pattern to controllably cure the selected regions of the layer to facilitate forming a plurality of piezoelectric transducer posts. The piezoelectric transducer posts include a plurality of spatial positions located on an X-Y plane of the substrate and having a plurality of shapes in an X-Y-Z plane of the substrate. The piezoelectric transducer posts are configured to facilitate minimizing shear waves and maintaining longitudinal waves within the ultrasound probe.

Still further in an aspect, an ultrasound probe is provided. The probe includes a substrate and a plurality of piezoelectric transducer posts controllably formed on the substrate. The posts are formed in a plurality of spatial positions on an X-Y plane of the substrate, wherein the plurality of piezoelectric posts includes a plurality of shapes defined in an X-Y-Z plane of the substrate. The plurality of piezoelectric transducer posts are configured to facilitate minimizing shear waves and maintaining longitudinal waves within the ultrasound probe. The probe further includes a filler circumscribed around the piezoelectric transducer posts on the substrate. Electrical contacts are coupled to the plurality of piezoelectric transducer posts to facilitate converting electrical energy into ultrasonic energy.

DETAILED DESCRIPTION OF THE INVENTION

Figure 1:
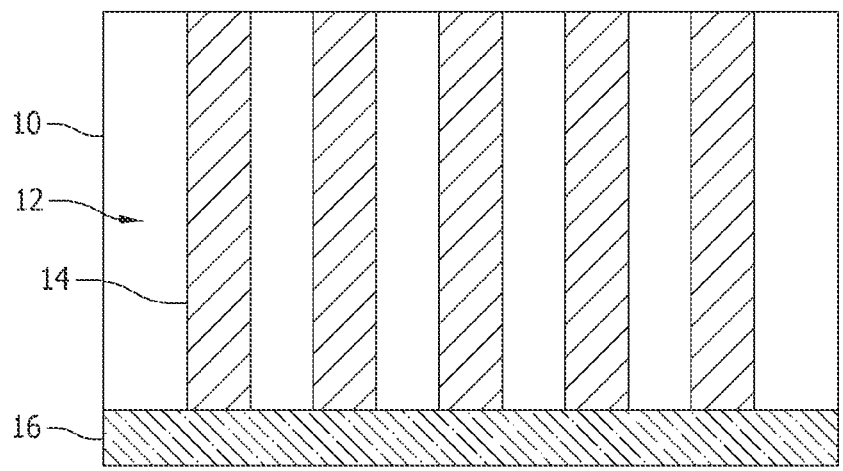
FIG. 1 illustrates a partial cross-sectional view of an exemplary transducer structure that includes an array of a plurality of transducer posts.
Figure 2:
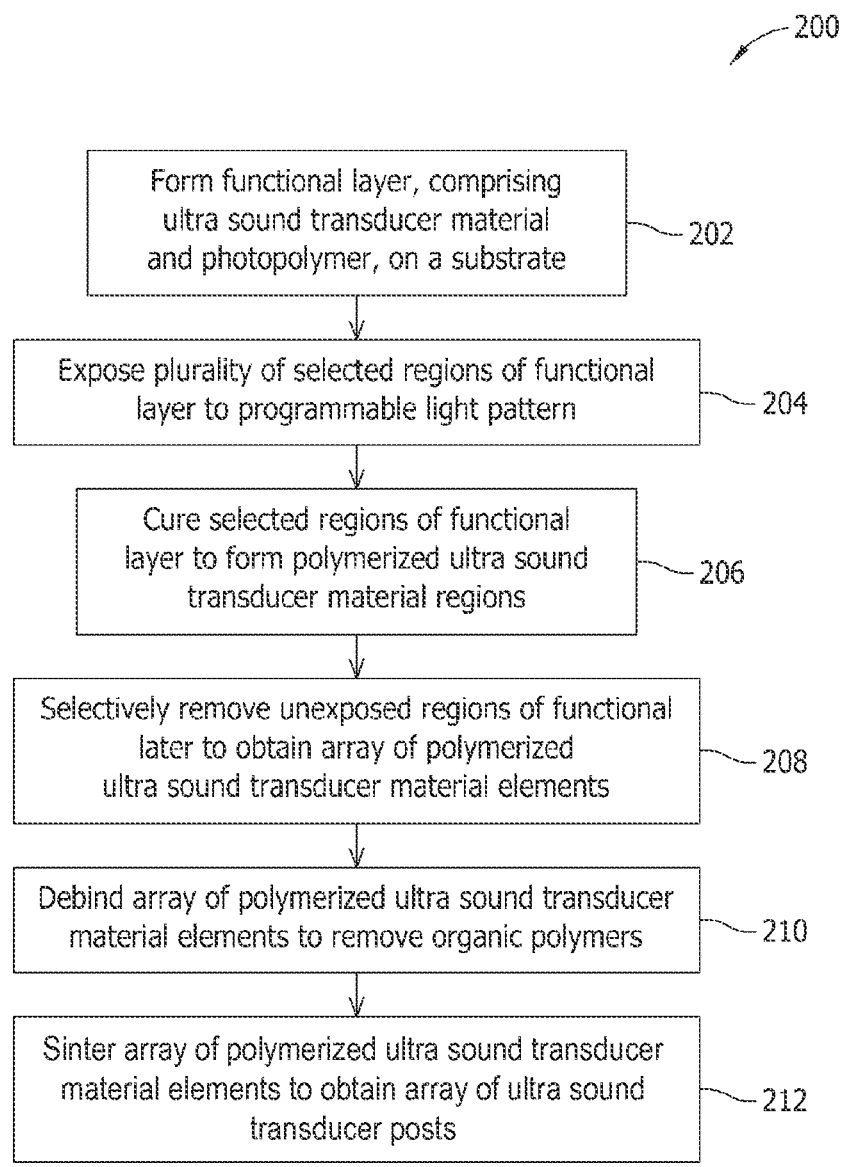
FIG. 2 is a flow chart of an exemplary method of manufacturing an array of transducer posts used with the structure shown in FIG. 1.

FIG. 1 illustrates a cross sectional view of an exemplary transducer structure 10 that includes an array 12 of a plurality of transducer posts 14 disposed on a substrate 16. FIG. 2 is a flow chart of an exemplary method 200 that may be used to fabricate array 12 of transducer posts 14. In the exemplary embodiment, method 200 includes forming 202 a layer 18 (shown in FIG. 3) on substrate 16. Substrate 16 may include materials such as, but not limited to, plastic, glass, mica, metals, ceramics, and/or combinations thereof. Layer 18 is fabricated from materials such as, but not limited to, an ultrasound transducer material, and a photo-curable, polymer material. Ultrasound transducer material may include one or more conductive materials, and/or one or more piezoelectric materials and/or one or more acoustic materials.

Figure 4:
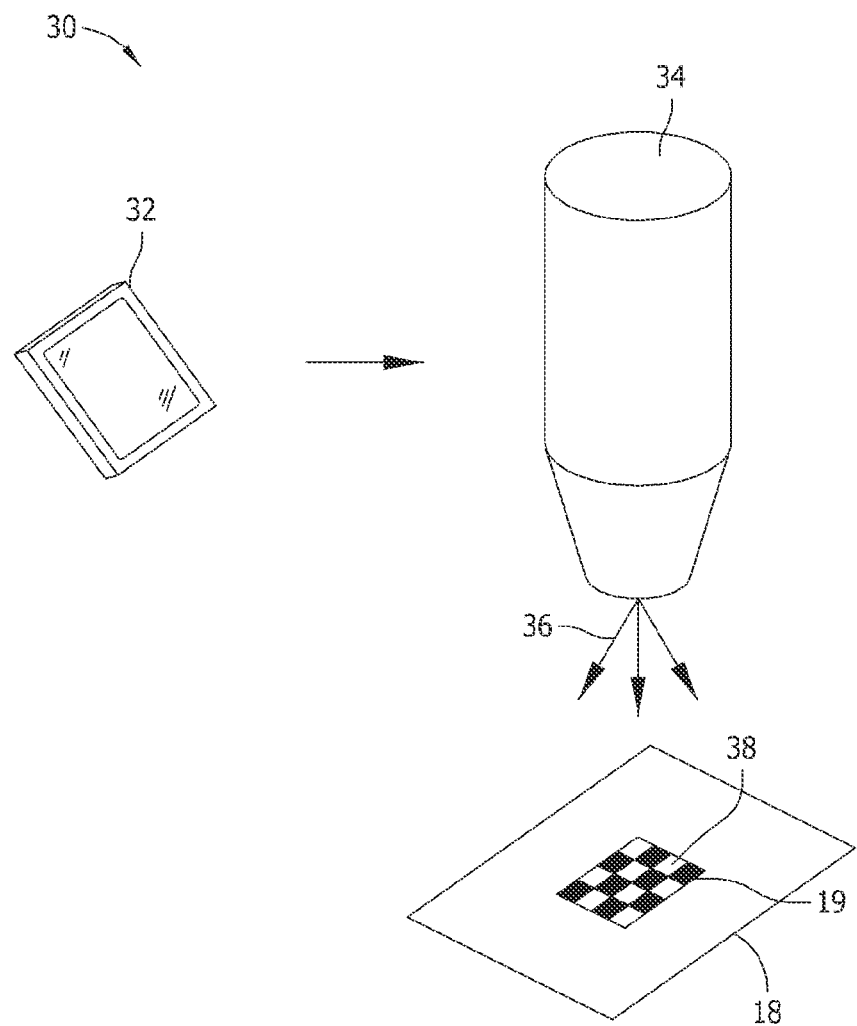
FIG. 4 illustrates an exemplary light modulating system that may be used in manufacturing transducer posts used with the structure shown in FIG. 1.
Figures 5A, 5B, 5C:
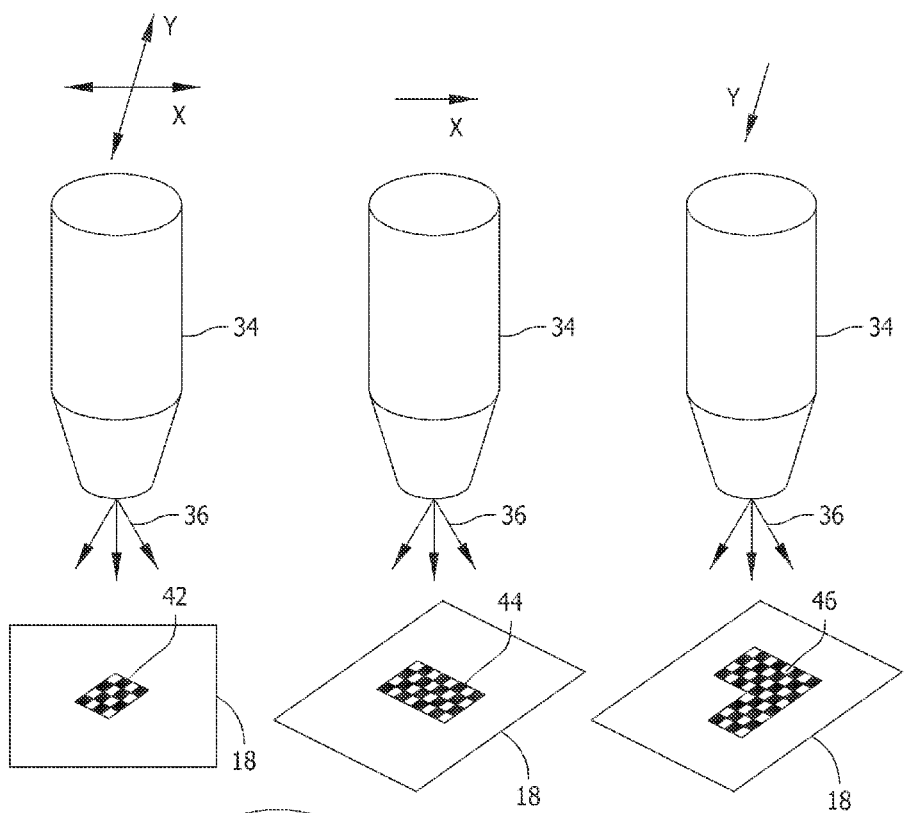
FIG. 5A illustrates the light modulating system shown in FIG. 4 being used to fabricate an exemplary light pattern.
FIG. 5B illustrates another process view of the light modulating system shown in FIG. 4.
FIG. 5C illustrates another process view of the light modulating system shown in FIG. 4.
Figure 5D:
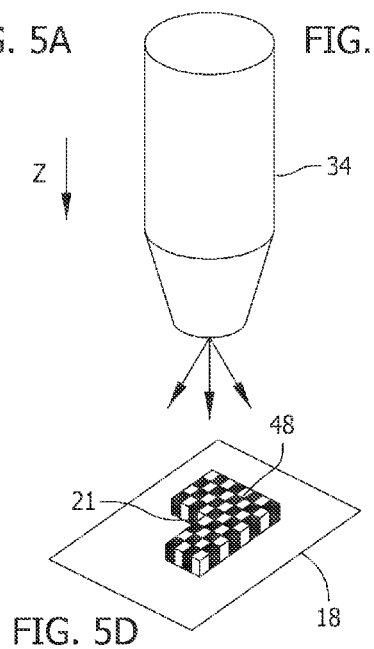
FIG. 5D illustrates another process view of the light modulating system shown in FIG. 4.

In the exemplary embodiment, a plurality of selected regions of layer 18 is exposed 204 to a programmable light system 30 (shown in FIG. 4). Next, selected regions of layer 18 are cured 206 to form polymerized ultrasound transducer regions and unexposed regions of layer 18 are selectively removed 208 to create a desired arrangement of polymerized ultrasound transducer posts 14. Method 200 also includes debinding 210 polymerized ultrasound transducer posts 14 to selectively remove organic polymers, and then sintering 212 the arrangement of polymerized ultrasound transducer posts 14 to obtain a desired array 12 of ultrasound transducer posts 14.

Figure 3A:
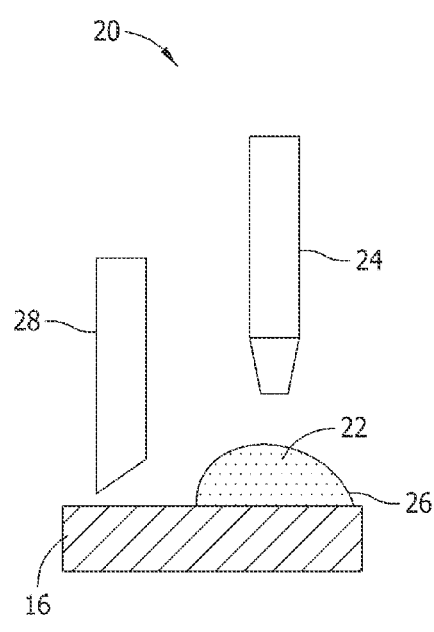
FIG. 3A illustrates an exemplary slurry system that may be used in manufacturing transducer posts used with the structure shown in FIG. 1.
Figure 3B:
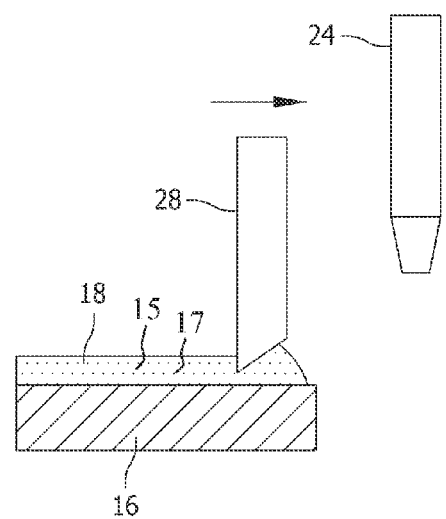
FIG. 3B illustrates another process view of the slurry system shown in FIG. 3A.

FIG. 3A illustrates an exemplary slurry system 20 that may be used in preparing layer 18. FIG. 3B illustrates another process view of the slurry system shown in FIG. 3A. Any suitable manufacturing method for forming thin uniform layers may be used to form layer 18. In the exemplary embodiment, dispenser 24 of slurry system 20 deposits a bead 26 of slurry 22 on substrate 16, wherein slurry 22 includes the transducer material and photopolymer material. A size of slurry bead 26 and/or a rate of bead 26 formation may be controlled based on predetermined characteristics of structure 10. During manufacture, a blade 28 controllably wipes slurry 22 to facilitate forming layer 18 with desired sizing and shaping. Other suitable systems (not shown) for use in preparing layer 18 include, but are not limited to, a knife blade technique, a doctor blade technique, and screen printing known in the art.

In the exemplary embodiment, layer 18 includes piezoelectric material 15 and photo-curable, polymer material 17. Any suitable piezoelectric material may be used in fabricating layer 18. For example, piezoelectric materials may include, but are not limited to only including, lead zirconate titanate, lead metaniobate, lithium niobate, bismuth titanate, lead titanate, and/or combinations thereof. Other piezoelectric materials may include, but are not limited to only including, lead magnesium niobate, lead zinc niobate, lead nickel niobate, bismuth scandium oxide, and/or combinations thereof. In the exemplary embodiment, the piezoelectric material includes lead zirconate titanate (PZT). In another embodiment, layer 18 may also include any suitable conductive material and a photopolymer. For example, a suitable conductive material may include, but is not limited to only including, platinum, palladium, platinum-palladium alloys, and/or combinations thereof. Any photo-curable polymer that is compatible with the one or more ultrasound transducer materials used to form layer 18. Further, any photo-curable material that polymerizes when exposed to a light of a given wavelength distribution may be used to fabricate layer 18.

FIG. 4 illustrates an exemplary light modulator system 30 that may be used in manufacturing an array 12 of transducer post 14 used with structure 10. FIGS. 5a-5d illustrate light modulating system shown in FIG. 4 being used to fabricate an exemplary light pattern. In an embodiment, a spatial light modulator 34 is systematically moved to expose layer 18, using a "step-and-scan" manufacturing technique. During manufacturing, a plurality of selected regions 19 of layer 18 are exposed 204 to light of a predetermined intensity and wavelength distribution that is capable of initiating a polymerization process. System 30 includes a computer 32 that provides digital control signals to control the modulating light intensity and/or direction of spatial light modulator 34 to facilitate generating a predetermined light pattern 36 on layer 18. In one embodiment, programmable light pattern 36 is digitally controlled. Computer 32 generates electronic control signals and spatial light modulator 34 projects predetermined light pattern 36 on the plurality of selected regions 19 of layer 18 to expose and to cure 206 those selected regions 19 of layer 18. Each layer 18 is exposed to the digitally, programmable light pattern 36, and the imaging of individual features is dynamically achieved via computer control. A digital pattern 38 representing the cross-section of the structure to be fabricated is projected onto layer 18. Spatial light modulator 34 selectively cures 206 the photopolymer present within the selected region 19 of layer 18 to yield polymerized regions within layer 18.

As best seen in FIGS. 5A-5D, during manufacture spatial light modulator module 34 is movable in a generally horizontal plane along the X- and Y-planes to emit the digitally programmable light pattern 36 in a desired exposure pattern 42 on layer 18. Spatial light modulator module 34 may also be movable along the Z-plane. For example, spatial light modulator module 34 may be translated along the X-plane to produce a first exposure pattern 44 over at least a portion of layer 18, and translated along the Y-plane to produce a different exposure pattern 46 on at least a portion of layer 18. Similarly, spatial light modulator 34 may be translated along the Z-plane to produce yet another exposure pattern 48 on at least a portion of layer 18. The use of this step-and-scan technique facilitates larger portions being fabricated using small area, high resolution, and digital masks.

Method 200 continues to selectively remove 208 unexposed regions 21 of layer 18 to produce a desired arrangement of polymerized transducer posts 14. Next, array 12 of polymerized transducer posts 14 is debinded 210 to remove organic polymers. Finally, in the exemplary embodiment, method 200 includes sintering 212 polymerized transducer posts 14 to obtain desired array 12 of ultrasound transducer posts 14 spaced across substrate 16 (as shown in FIG. 1). Transducer posts 14 can be placed at any controlled spacing and/or can be fabricated independently with different physical dimensions and/or different shapes. Transducer posts 14 can be controllably formed at reduced costs with any spacing and/or have any physical dimensions and/or shapes for freeform, three dimensional formation that enables structure 10 to function as described herein.

The controllable formation and arrangement of transducer posts 14 facilitates enhanced resolution by a probe (such as probe 50 shown in FIG. 11) by minimizing or substantially eliminating shear waves of ultrasound transducer wavelengths traveling within array 12. Transducer posts 14 may have any suitable configuration, and/or orientation and/or sizing that facilitate minimizing or eliminating shear waves within array 12; that facilitates maintaining and/or enhancing longitudinal waves within array 12 and/or that facilitates enhancing resolution by probe 50.

In an embodiment, plurality of transducer posts 14 are controllably formed and arranged on substrate 16. The plurality of transducer posts 14 are formed having a plurality of spatial positions located on the X-Y plane of substrate 16. Further, the plurality of transducer posts 14 are formed having a plurality of shapes defined in the X-Y-Z plane of substrate

16. The plurality of spatial positions and the plurality of shapes of transducer posts 14 are configured to facilitate minimizing shear waves and maintaining longitudinal waves within array 12. In an embodiment, spatial positions and/or shapes of transducer posts 14 are configured to facilitate interference and/or cancellation of shear waves generated by posts 14 and traveling within or among posts 14. In the exemplary embodiment, spatial positions and/or shapes of transducer posts 14 further facilitate reducing amplitude of shear waves traveling within or among posts 14. The plurality of spatial positions and shapes facilitate enhancing piezoelectric properties and acoustic properties of a probe, such as probe 50 (shown in FIG. 11).

Figure 6:
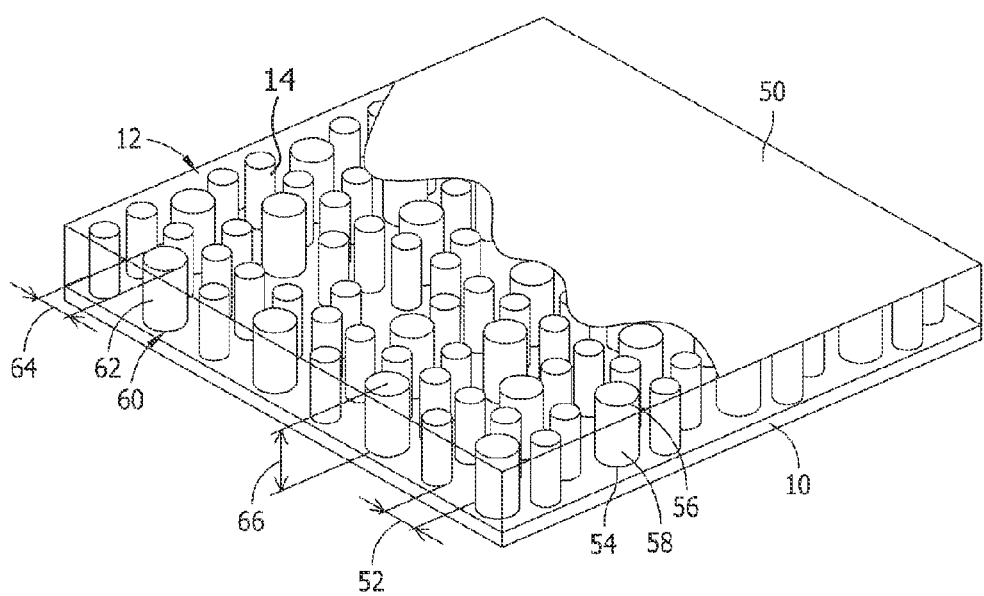
FIG. 6 illustrates a perspective view of the structure shown in FIG. 1.

FIG. 6 illustrates a perspective view of structure 10 including controllably formed and arranged array 12 of transducer posts 14. In an embodiment, the plurality of spatial positions of transducer posts 14 includes a periodic arrangement of the plurality of transducer posts 14 on substrate 16. Alternatively, the plurality of spatial positions of transducer posts 14 includes an aperiodic arrangement of the plurality of transducer posts 14 on substrate 16. In an embodiment, the plurality of spatial positions of transducer posts 14 located on substrate 16 includes at least one of a 0-3, 3-0, 1-3, 3-1, 3-3 and 2-2 composite structure.

In the exemplary embodiment, transducer posts 14 are positioned such that a spacing 52 is defined between adjacent transducer posts 14. In an embodiment, spacing 52 is equidistant among at least one of the transducer posts 14 and adjacent transducer posts 14. In another embodiment, spacing 52 is non-equidistant among at least one of the transducer posts 14 and adjacent transducer posts 14. In one embodiment, spacing 52 between transducer posts 14 is between about 5 microns to about 50 microns. Each transducer post 14 includes a proximal end 54, a distal end 56, and a body 58 that extends there between. Proximal end 54 is coupled to substrate 16, and body 58 extends from proximal end 54 away from substrate 16. In the exemplary embodiment, at least one of the plurality of transducer posts 14 has a body 58 that is formed with a substantially uniform configuration 60. More specifically, as used herein, uniform configuration 60 includes a substantially smooth side profile and/or a substantially uniform patterned side profile (not shown) that accommodates minor variations in cross-sectional shape along body 58. Further, as used herein, uniform configuration 60 includes substantially similar cross sectional areas for bodies 58.

In another embodiment, the plurality of shapes for the plurality of transducer posts 14 includes a different cross sectional area for at least one transducer post 14 of the plurality transducer posts 14. Still further, in an embodiment, the plurality of shapes for the plurality of transducer posts 14 includes a different side profile shape for at least one transducer post 14 of the plurality of transducer posts 14.

In the exemplary embodiment, at least one body 58 of the plurality of transducer posts 14 has a non-orthogonal shape 62 such as, but not limited to, a columnar shape including a substantially circular cross section. In one embodiment, a diameter 64 of such a transducer element 14 is between about 1 micron to about 50 microns in length. In the exemplary embodiment, bodies 58 each have a substantially equal height 66 as measured between ends 54 and 56. In the exemplary embodiment, each transducer element height 66 is between about 5 microns to about 150 microns. Moreover, in the exemplary embodiment, body 58 includes a height to width aspect ratio of at least 2:1. Alternatively, at least one body 58 is formed with a different height 66 as compared to other bodies 58 in the plurality of transducer posts 14 within array 12.

Figure 7:
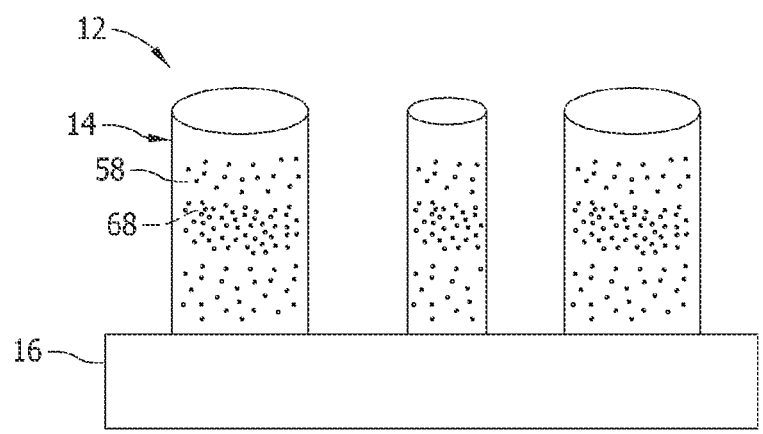
FIG. 7 illustrates a side view of exemplary transducer posts for the structure shown in FIG. 6.

FIG. 7 illustrates a side view of exemplary transducer posts 14 for the structure shown in FIG. 6. In the exemplary embodiment, at least one transducer post 14 can have a different density 68 than other transducer posts 14 of the plurality of transducer posts 14. Alternatively, each transducer post 14 of the plurality of transducer posts 14 can have substantially similar densities. The density structure of each transducer post 14 facilitates minimizing or substantially eliminating shear waves of ultrasonic transducer waves traveling within array 12. Transducer post 14 can be formed with any density distribution that facilitates eliminating shear waves from traveling within, or among posts 14 of array 12. Transducer post 14 can be formed with any density distribution that facilitates maintaining longitudinal waves of waves traveling within, or among, posts 14 of array 12. Further, in an embodiment, each transducer post 14 of the plurality of transducer posts 14 can have a uniform density distribution or a non-uniform density distribution. Transducer post 14 can also include structures such as, but not limited to, blind holes and thru-holes distributed within transducer post 14.

Figure 8:
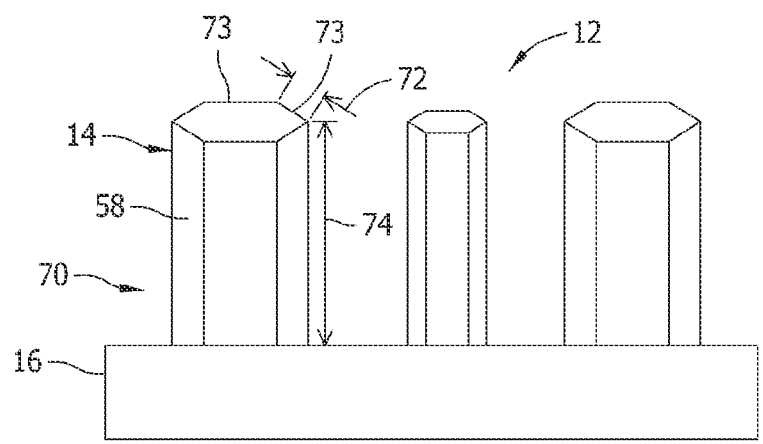
FIG. 8 illustrates another side view of exemplary transducer posts that may be used with the structure shown in FIG. 6.

FIG. 8 illustrates a side view of an exemplary transducer element 14 formed with a non-orthogonal shape 70. In the exemplary embodiment, transducer element 14 is formed with a columnar shape that is defined by a hexagonal cross section. In the exemplary embodiment, a length 72 of each side 73 of transducer element 14 is between about 1 micron to about 50 microns, and each transducer element 14 has a height 74 as measured from substrate 16 of between about 5 microns to about 150 microns.

Figure 9:
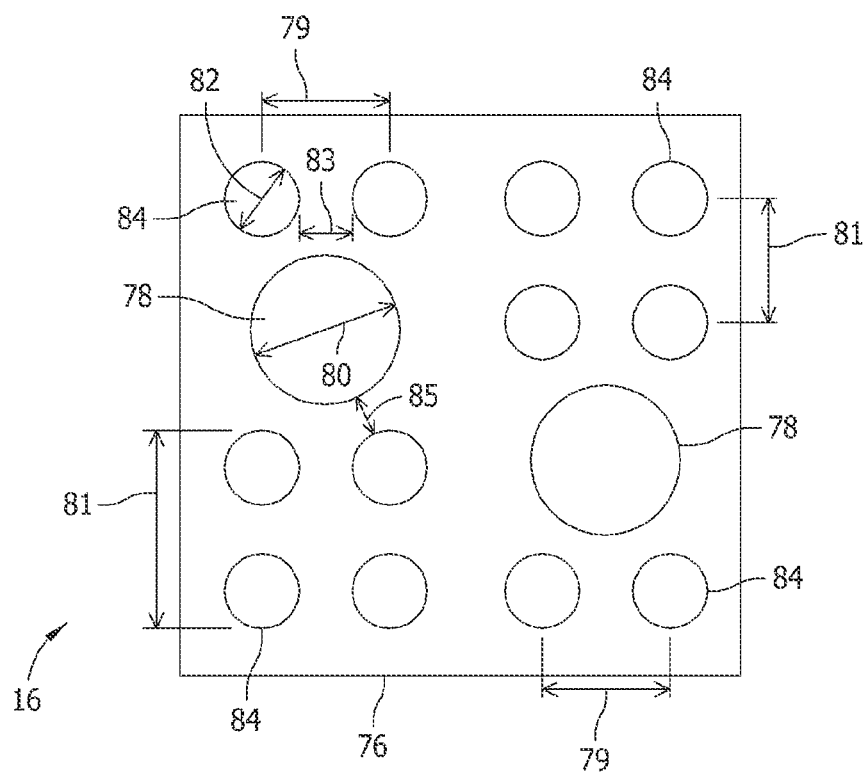
FIG. 9 illustrates a plan view of an exemplary array of transducer posts that may be used with the structure shown in FIG. 6.
Figure 10:
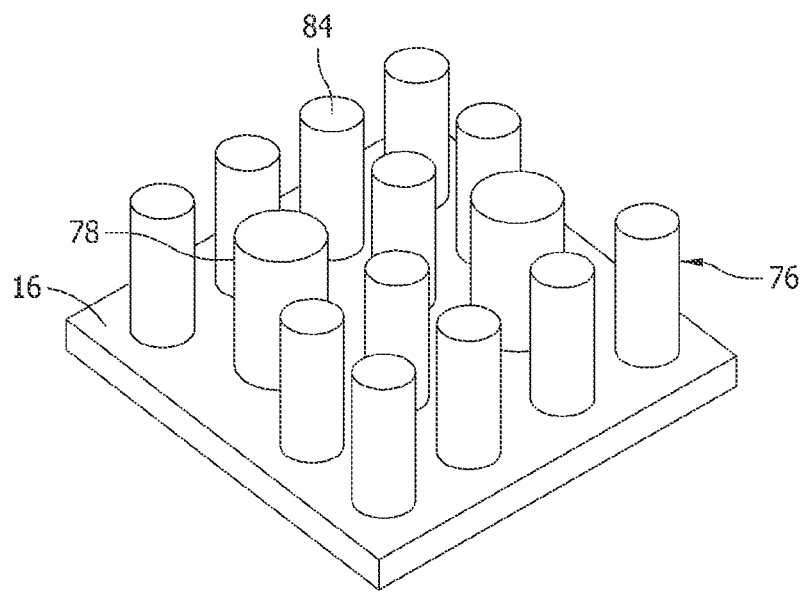
FIG. 10 illustrates a perspective view of the array of transducer posts shown in FIG. 9.

FIG. 9 illustrates a plan view of an exemplary array 76 of transducer posts 14 disposed on substrate 16 shown in FIG. 6. FIG. 10 illustrates a perspective view of array 76. In the exemplary embodiment, transducer posts 14 within array 76 are formed with a non-orthogonal shape, such as, but not limited to, a columnar shape defined by a substantially circular cross section. Alternatively, transducer posts 14 in array 76 can be formed with other non-orthogonal shapes (not shown) such as, but not limited to, hexagonal cross-sectional shapes. Moreover, transducer posts 14 in array 76 may be formed with orthogonal shapes (not shown).

As shown, at least some transducer posts 14 are formed with different physical sizing within array 76, as compared to other transducer posts 14 within array 76. More specifically, in the exemplary embodiment, array 76 includes a plurality of transducer posts 78 that are formed with a larger cross sectional size as compared to other transducer posts 84 in array 76. Moreover, in an embodiment, each transducer element 78 within array 76 has a larger diameter 80 than a diameter 82 of each adjacent transducer element 84. In the exemplary embodiment, each diameter 80 is approximately 30% to 50% larger than each diameter 82.

In array 76, each transducer element 78 is positioned between a pair 79 of transducer posts 84 and a grouping 81 of other transducer posts 84. Grouping 81 of transducer posts 84 may include a plurality of transducer posts 84. In one embodiment, grouping 81 includes four transducer posts 84. In the exemplary embodiment, spacing 83 defined between adjacent transducer posts 84 is between about 5 microns to about 50 microns. Further, spacing 85 defined between transducer element 78 and each adjacent transducer element 84 is between about 5 microns to about 50 microns. The orientation of array 76, and the shape and/or size of transducer posts 78 and 84 facilitate minimizing or substantially eliminating shear waves from traveling within, or among, transducer posts 14 of transducer structure 10. Further, the orientation of array 76, and the shape and/or size of transducer posts 78 and 84 facilitate maintaining longitudinal waves traveling within, or among, transducer posts 14 of transducer structure 10. Additionally, the orientation of array 76, and the shape and/or size of transducer posts 78 and 84 facilitate reducing an overall size of structure 10 to enable probe, such as probe 50 (shown in FIG. 11), to operate at higher frequencies than probes with known spacing and/or orientation and/or shapes. Further, the orientation of array 76, and the shape and/or size of transducer posts 78 and 84 facilitate increasing the resolution in images obtained by probe 50.

Figure 11:
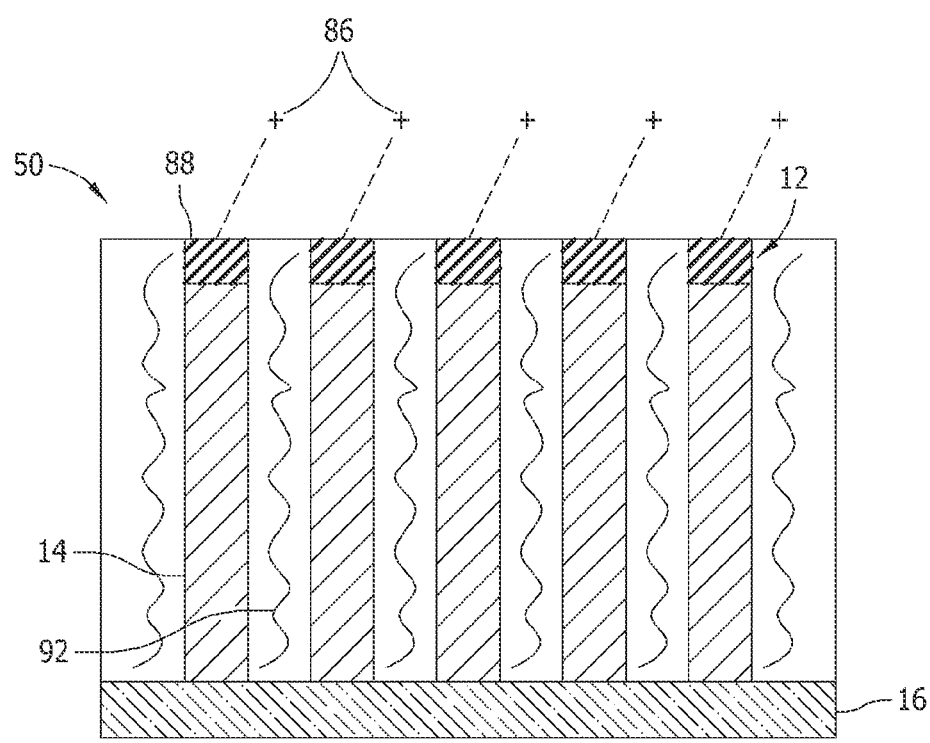
FIG. 11 illustrates a partial side view of an exemplary probe fabricated with an array of transducer posts.

FIG. 11 illustrates a partial side view of exemplary probe 50 fabricated with array 12 of transducer posts 14. Probe 50 includes array 12 of transducer posts 14 with electrodes 86 coupled on each top side 88 that enable probe 50 to be electrically coupled to a power source (not shown). Posts 14 convert electrical energy into ultrasonic energy. Probe 50 also includes a filler 92 that circumscribes the plurality of transducer posts 14 on substrate 16. In the exemplary embodiment, filler 92 includes an epoxy material that holds the transducer posts together and supports the electrode material between post 14, which creates a composite material with a lower acoustic impedance as compared to monolithic ceramic materials and higher coupling factor. This formation allows for a more efficient acoustic coupling between the transducer post 14 and the component (not shown) being inspected by probe 50.

As used herein, the term "controlled or arranged," when used in the context of a discussion of one or more components of the structure and/or transducer post and/or probe, may refer to a physical geometry and/or a size and/or an orientation of the transducer posts as is independently user-defined or programmably implemented. In addition, the term may also refer to, and include the situation wherein the arrangement of the transducer posts of the probe is also user-defined, and may be, for instance, non-uniform and/or uniform. This arrangement could be aperiodic/random over controlled or uncontrolled distances. The term "post" when used in the context of a discussion of one or more components of the structure and/or transducer post and/or probe, may refer to any features of piezoelectric materials.

The embodiments described herein provide geometries and/or orientations and/or spacings for transducer posts to facilitate minimizing and/or eliminating shear waves and maintaining longitudinal waves, which in turn, enhances the performance of the associated probe, as compared to the performance of probes that include known transducer posts. The embodiments described herein include non-orthogonal column cross-sections in either the x-y, x-z, or y-z planes such as, for instance, circular and hexagonal. Non-orthogonal cross sections further facilitate minimizing or substantially eliminating shear waves that are generated by the application of an electrical potential across the structure. The embodiment described herein further provide the ability to produce free-form, three dimensional transducer posts for improved higher electromechanical coupling coefficients, improved acoustic impedance match between the transducer and the article being inspected, and improved resonance characteristics using cost effective manufacturing.

The embodiments described herein provide a structure for use with a transducer probe. The disclosed dimensional ranges include all sub ranges there between. The dimensional ranges for the transducer posts facilitate reducing an overall size of the transducer element to enable the probe to be operated at higher frequencies. Additionally, the dimensional ranges for the transducer element facilitate increasing resolution in images obtained by probe.

A technical effect of the of the embodiments described herein includes the controlled array of transducer posts which facilitates minimizing or eliminating shear waves traveling within array of transducer structure. Another technical effect of the array of transducer posts described herein facilitates reducing the size of the transducer element to facilitate operating the probe at higher frequencies. A further technical effect technical effect of the array of transducer posts facilitates increasing resolution in images obtained by probe.

Exemplary embodiments of a transducer post, probe, and methods of manufacturing the transducer post, structure, and probe and assembling the probe are described above in detail. The transducer post, structure, probe, and methods are not limited to the specific embodiments described herein, but rather, components of the transducer post and/or the probe and/or steps of the method may be utilized independently and separately from other components and/or steps described herein. For example, the probe and methods may also be used in combination with other diagnostic systems and methods, and are not limited to practice with only the ultrasonic transducer probe as described herein. Rather, the exemplary embodiments can be implemented and utilized in connection with many other diagnostic systems or other support structures.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best wave, and also to enable any person skilled in the art to practice the invention, including making and using any layers or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A composite ceramic transducer structure for use in the construction of an ultrasound probe, the composite ceramic transducer structure comprising:
    a substrate; and
    a plurality of piezoelectric transducer posts controllably formed on the substrate in a plurality of spatial positions located on an X-Y plane of the substrate, the plurality of piezoelectric posts comprising a plurality of shapes defined in an X-Y-Z plane of the substrate, the plurality of piezoelectric transducer posts are configured to facilitate minimizing shear waves within the ultrasound probe, wherein at least one of the plurality of piezoelectric transducer posts comprises a non-uniform density.

2. The composite ceramic transducer structure of claim 1, wherein each of the plurality of piezoelectric transducer posts comprises a photo curable piezoelectric ceramic material.

3. The composite ceramic transducer structure of claim 1, wherein the plurality of spatial positions located on the X-Y plane of the substrate comprise a 1-3 composite structure.

4. The composite ceramic transducer structure of claim 1, wherein the plurality of spatial positions in the X-Y plane of the substrate comprise an aperiodic arrangement of the plurality of piezoelectric transducer posts.

5. The composite ceramic transducer structure of claim 1, wherein at least one of the plurality of piezoelectric transducer posts comprises a different cross sectional area than the others of the plurality of piezoelectric transducer posts.

6. The composite ceramic transducer structure of claim 1, wherein at least one of the plurality of piezoelectric transducer posts comprises a different side profile than the others of the plurality of piezoelectric transducer posts.

7. The composite ceramic transducer structure of claim 1, wherein at least one of the plurality of piezoelectric transducer posts comprises a different height than the others of the plurality of piezoelectric transducer posts.

8. The composite ceramic transducer structure of claim 1, wherein at least one of the plurality of piezoelectric transducer posts comprises a different density than the others of the plurality of piezoelectric transducer.

9. The composite ceramic transducer structure of claim 1, wherein at least one of the plurality of piezoelectric transducer posts comprises a blind hole, a thru-hole, or any combination thereof.

10. The composite ceramic transducer structure of claim 1, wherein at least one of the plurality of piezoelectric transducer posts is spaced non-equidistant from adjacent piezoelectric transducer posts of plurality of piezoelectric transducer posts.

11. The composite ceramic transducer structure of claim 1, wherein at least one of the plurality of piezoelectric transducer posts comprises a height to width aspect ratio of at least 2:1.

12. A method for manufacturing a ceramic transducer structure for use in the construction of an ultrasound probe, the method comprising:
    forming a substrate layer;
    forming a layer on the substrate layer, the layer comprising a transducer material and a photopolymer; and
    exposing a plurality of selected regions of the layer to a programmable light pattern to controllably cure the selected regions of the layer to facilitate forming a plurality of piezoelectric transducer posts having a plurality of spatial positions located on an X-Y plane of the substrate and having a plurality of shapes in an X-Y-Z plane of the substrate, the piezoelectric transducer posts are configured to facilitate minimizing shear waves and maintaining longitudinal waves within the ultrasound probe, and at least one of the plurality of piezoelectric transducer posts comprises a non-uniform density.

13. The method of claim 12, wherein controllably curing the selected regions of the layer to facilitate forming the plurality of piezoelectric transducer posts comprises forming the plurality of shapes having a different cross sectional area for at least one piezoelectric transducer post of the plurality of piezoelectric transducer posts.

14. The method of claim 12, wherein controllably curing the selected regions of the layer to facilitate forming the plurality of piezoelectric transducer posts comprises forming at least one of the plurality of piezoelectric transducer posts with a different side profile than the others of the plurality of piezoelectric transducer posts.

15. The method of claim 12, wherein controllably curing the selected regions of the layer to facilitate forming the plurality of piezoelectric transducer posts comprises forming at least one of the plurality of piezoelectric transducer posts with a different density than the others of the plurality of piezoelectric transducer posts.

16. The method of claim 12, wherein controllably curing the selected regions of the layer to facilitate forming the plurality of piezoelectric posts comprises forming at least one the plurality of piezoelectric transducer posts non-equidistant from adjacent piezoelectric transducer posts of the plurality of piezoelectric transducer posts.

17. The method of claim 12, further comprising depositing a filler circumscribed around the plurality of piezoelectric transducer posts.

18. An ultrasound probe, the probe comprising:
    a substrate;
    a plurality of piezoelectric transducer posts controllably formed on the substrate in a plurality of spatial positions on an X-Y plane of the substrate, the plurality of piezoelectric posts comprising a plurality of shapes defined in an X-Y-Z plane of the substrate, the plurality of piezoelectric transducer posts are configured to facilitate minimizing shear waves and maintaining longitudinal waves within the ultrasound probe, wherein at least one of the piezoelectric transducer posts comprises a non-uniform density;
    a filler circumscribed around the piezoelectric transducer posts on the substrate; and
    an electrical contact coupled to the plurality of piezoelectric transducer posts to facilitate converting electrical energy into ultrasonic energy.

19. The ultrasound probe of claim 18, wherein the plurality of spatial positions in the X-Y plane of the substrate comprises an aperiodic arrangement of the plurality of piezoelectric transducer posts.

20. The ultrasound probe of claim 18, wherein at least one of the plurality of piezoelectric transducer posts comprises a different cross sectional area than the others of the plurality of piezoelectric transducer posts.

* * * * *